(12) United States Patent
Sapian

(10) Patent No.: US 7,300,282 B2
(45) Date of Patent: Nov. 27, 2007

(54) BIOFUNCTIONAL DENTAL IMPLANT

(76) Inventor: Schubert L. Sapian, P.O. Box 16310, Fort Worth, TX (US) 76162

( * ) Notice: Subject to any disclaimer, the term of this patent is extended or adjusted under 35 U.S.C. 154(b) by 429 days.

(21) Appl. No.: 10/892,502

(22) Filed: Jul. 16, 2004

(65) Prior Publication Data

US 2006/0014120 A1 Jan. 19, 2006

(51) Int. Cl.
*A61C 8/00* (2006.01)

(52) U.S. Cl. ...................... 433/173; 433/169

(58) Field of Classification Search ........... 433/169, 433/172, 173, 174, 177
See application file for complete search history.

(56) References Cited

U.S. PATENT DOCUMENTS

| | | | | |
|---|---|---|---|---|
| 2,258,207 | A * | 10/1941 | Irwin | 433/173 |
| 3,708,883 | A * | 1/1973 | Flander | 433/174 |
| 4,318,696 | A * | 3/1982 | Kasama et al. | 433/173 |
| 4,850,870 | A * | 7/1989 | Lazzara et al. | 433/174 |
| 4,957,437 | A * | 9/1990 | Shimura et al. | 433/169 |
| 5,004,421 | A * | 4/1991 | Lazarof | 433/173 |
| 5,174,755 | A * | 12/1992 | Fukuda | 433/173 |
| 5,468,150 | A * | 11/1995 | Brammann | 433/173 |
| 5,782,918 | A * | 7/1998 | Klardie et al. | 606/60 |
| 5,890,902 | A * | 4/1999 | Sapian | 433/173 |
| 6,142,782 | A * | 11/2000 | Lazarof | 433/174 |
| 6,227,859 | B1 * | 5/2001 | Sutter | 433/173 |
| 6,939,135 | B2 * | 9/2005 | Sapian | 433/174 |

\* cited by examiner

*Primary Examiner*—Ralph A. Lewis
(74) *Attorney, Agent, or Firm*—Morland C. Fischer (57) ABSTRACT

A biofunctional dental implant wherein a crown portion is connected to a root portion without the use of the conventional short screws, or the like. A flexible abutment projects upwardly from the root portion, and the crown portion is positioned in surrounding engagement with the flexible abutment. A threaded abutment post is advanced through the flexible abutment and into receipt by the root portion. The advancement of the abutment post through the flexible abutment generates an outward pushing force for causing a plurality of flexible splines of the abutment to bend outwardly and into engagement with an elastomeric cap of the crown portion for holding the crown portion atop the root portion. In one preferred embodiment, a replacement crown portion is detachably connected to an existing root portion by way of a removable abutment screw so as to enable a broken or worn crown portion to be removed and replaced without the need for a new surgery.

23 Claims, 10 Drawing Sheets

BIOFUNCTIONAL DENTAL IMPLANT

BACKGROUND OF THE INVENTION

1. Field of the Invention

This invention relates to a biofunctional dental implant having a crown portion connected to a root portion by means of an abutment post. The advancement of the abutment post through a flexible abutment projecting upwardly from the root portion causes the flexible abutment to apply an outward pushing force against the crown portion for holding the crown portion atop the root portion without the use of screws or similar fastening devices.

2. Background Art

Natural teeth in the human mouth are supported in bone by periodontal fibers that function as shock absorbers when a compressive force is applied, such as during chewing. Through disease, accidental injury, anatomical abnormalities, age, and the like, a natural tooth may be removed or missing such that a dental appliance or prosthetic device (e.g., a crown) is implanted in the patient's bone structure to improve the patient's physical appearance and/or quality of mastication. However, problems such as crown breakage, screw loosening and screw breakage are inherent problems with the conventional crown implant.

More particularly, screws commonly associated with conventional crowns sometimes break because of over tightening and due to tension and lateral stress to which the crown is subjected during use. Moreover, a single crown can rotate in response to high lateral and torquing forces that are encountered while chewing, whereby to rotate and loosen screws. As dental professionals will understand, it is difficult and time consuming to retrieve and/or repair such broken screws. In addition, special purpose torque drivers are required to install these screws. Once the root portion of the implant is installed, it may take several months to achieve suitable bone integration of the root portion with the surrounding bone structure thereby resulting in increased loading time before the crown can be reliably attached. What is more, many crowns cannot easily absorb and distribute shock and other physical forces that are generated during chewing. Such crowns may be susceptible to damage or reduced life and may be unable to provide the function of a natural tooth and the quality of mastication associated therewith.

Accordingly, it would be desirable to overcome the problems associated with conventional crowns by avoiding screws which can break or loosen and eliminating the special purpose tools that are needed to install such screws. It would also be desirable to provide the crown with a shock absorbing cushion to better distribute the forces to which the crown will be subjected. It would be further desirable to have a replacement crown which is detachably connected to an existing root portion so that a new crown can be substituted for a defective or broken crown without requiring another surgery as well as the cost and patient discomfort associated therewith.

Reference may be made to my prior U.S. Pat. No. 5,890,902 issued Apr. 6, 1999 and pending patent application Ser. No. 10/159,644 filed Jun. 3, 2002 for examples of dental implants having a crown portion fixedly connected to a root portion.

SUMMARY OF THE INVENTION

A biofunctional dental implant is disclosed by which a crown portion is affixed to a root portion that is implanted below a dental patient's gum line within an implant socket that is formed in the patient's bone structure. The root portion may have one or more screw threads extending therearound, anti-rotational notches formed therein, and sharp edged barbs projecting therefrom by which to engage the patient's bone structure so as to anchor the root portion in place and prevent the root portion from rotating relative to the implant socket within which the root portion is located. A screw threaded channel runs longitudinally through the root portion and communicates with a set of radially extending ports so that a human growth factor and/or an antibiotic can be supplied to the implant socket within which the root portion is located. A flexible abutment stands upwardly from the top of the root portion. The flexible abutment has a plurality of flexible splines and a passageway that extends longitudinally between the splines. In the assembled configuration, the passageway extending through the flexible abutment is axially aligned with the channel extending through the root portion.

The crown portion includes a crown that is cemented over a metallic, ceramic or plastic coping. A shock absorbing elastomeric cap is positioned in surrounding engagement with the flexible abutment, and the combination crown and coping is positioned in surrounding engagement with the elastomeric cap. An abutment post having a threaded first end and a relatively wide head at the opposite end is advanced through the crown portion and into receipt by the axially aligned channel and passageway that extend longitudinally through the root portion and the flexible abutment, whereby the threaded end of the abutment post is moved into mating engagement with the screw threaded channel through the root portion.

In one embodiment, a spline spreader is positioned between the flexible splines of the flexible abutment for receipt of the threaded end of the abutment post. As the threaded end of the abutment post is advanced towards the root portion, the relatively wide head of the abutment post forces the spline spreader to slide over the flexible splines, whereby to generate a pushing force for causing the splines to rotate outwardly. Accordingly, the flexible splines compress the elastomeric cap against the crown and its coping to hold the crown portion atop the root portion.

In another embodiment, the flexible abutment is detachably connected to the top of the root portion so as to stand upwardly from a mounting hole formed therein. In this case, the relatively wide head of the abutment post has a tapered or angled area. The threaded end of the abutment post is advanced through the crown portion and into receipt by the axially aligned channel through the root portion and the passageway through the flexible abutment so as to connected the detachable abutment to the root portion. At the same time, the tapered area at the head of the abutment post slides over the flexible splines of the flexible abutment, whereby to generate the pushing force for causing the splines to rotate outwardly by which to compress the elastomeric cap against the crown portion and hold the crown portion atop the root portion.

In an additional embodiment, a replacement crown assembly is removably connected to an existing root portion that has been previously implanted within the patient's bone structure. A flexible abutment having a passageway extending longitudinally therethrough and a plurality of flexible splines is detachably connected to the existing root portion. The threaded end of a removable abutment post is advanced into receipt by the axially aligned channel through the root portion and the passageway through the flexible abutment so as to connect the detachable abutment to the existing root portion. The crown portion is located in surrounding engagement with the detachable flexible abutment. In this case, the relatively wide head of the removable abutment post is tapered. As the removable abutment post is advanced towards the root portion, the tapered head thereof slides over the flexible splines of the flexible abutment, whereby to generate the pushing force for causing the splines to rotate outwardly by which to compress the elastomeric cap against the crown portion and hold the crown portion atop the root portion.

DETAILED DESCRIPTION

Figure 1:
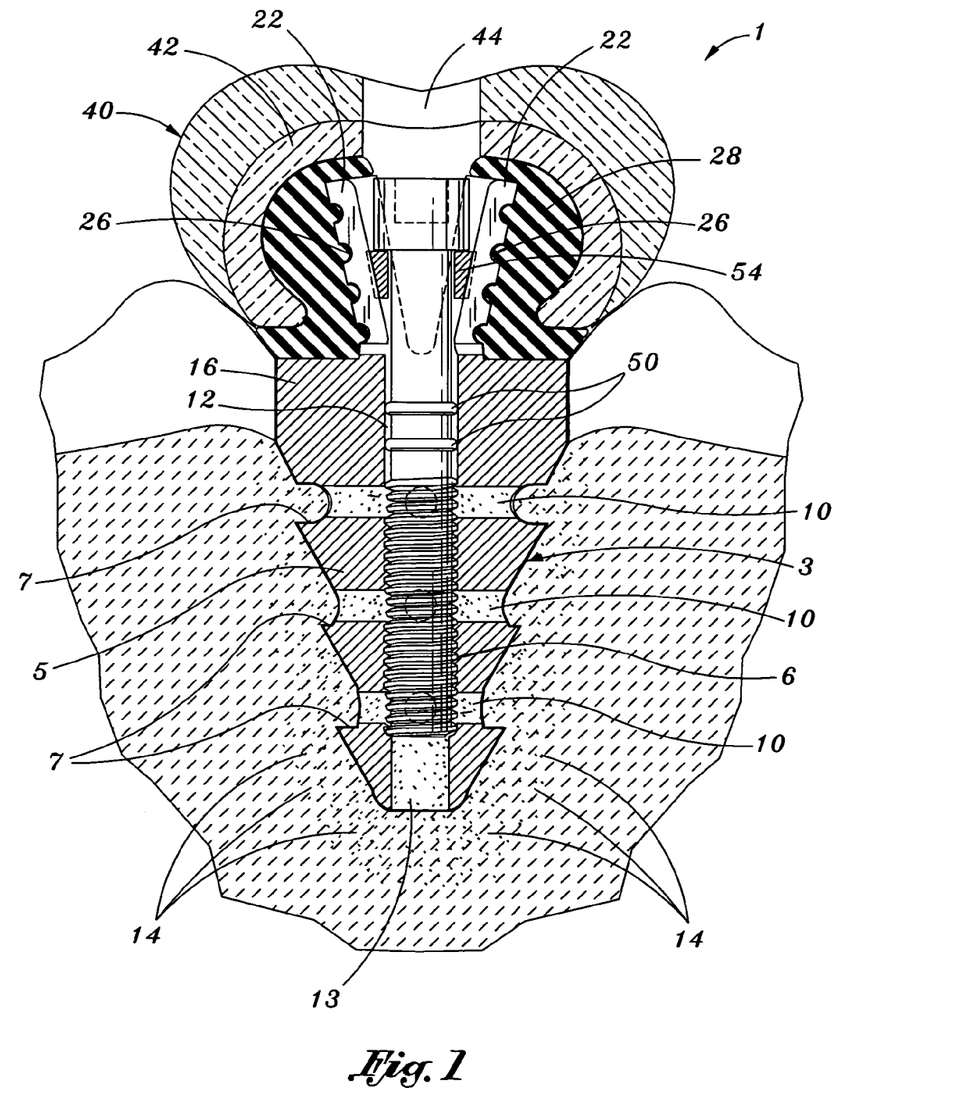
FIG. 1 is a cross-section showing a root portion and a crown portion of a biofunctional dental implant according to a first preferred embodiment connected to one another and implanted within the bone structure in the mouth of a dental patient.
Figure 2:
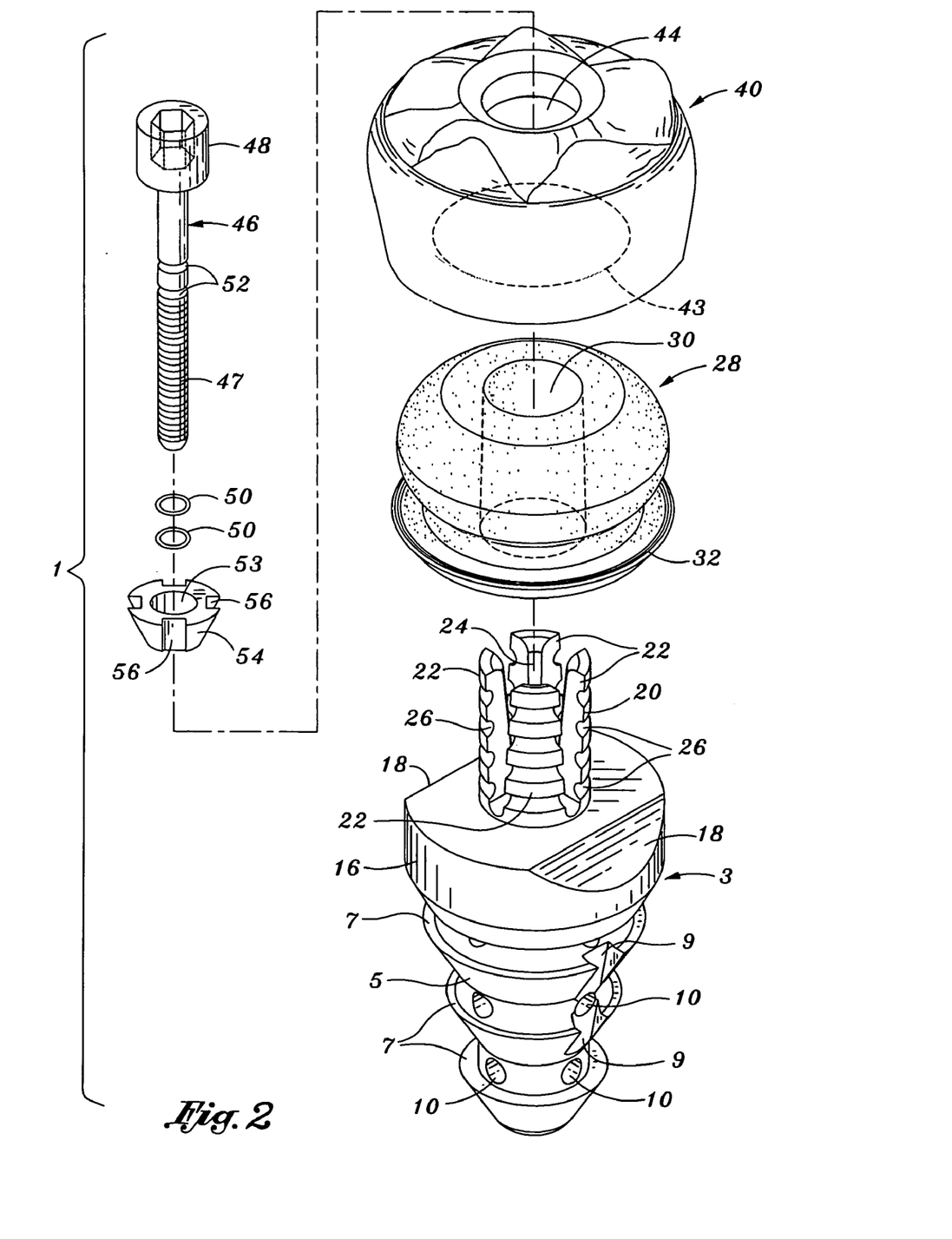
FIG. 2 is an exploded view of the dental implant shown in FIG. 1.
Figure 3:
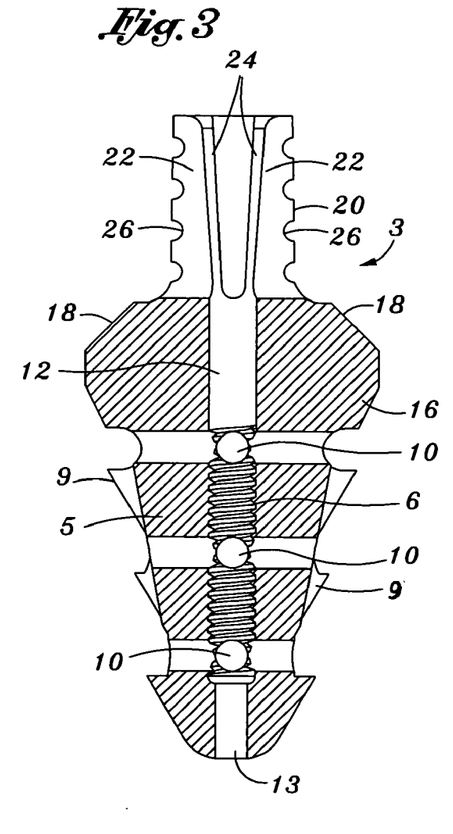
FIG. 3 is a cross-section of the root portion of the dental implant shown in FIG. 1.
Figure 4:
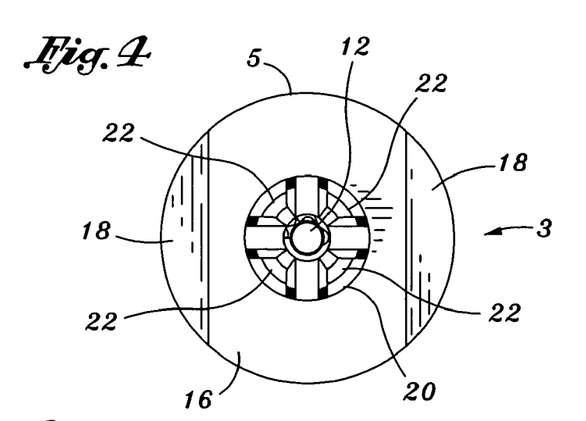
FIG. 4 illustrates a top view of the root portion for the dental implant shown in FIG. 1.
Figure 5:
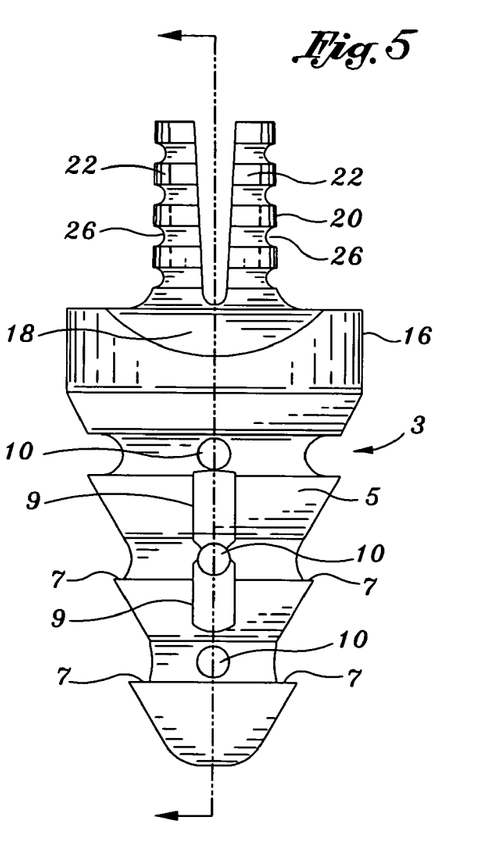
FIG. 5 illustrates a side view of the root portion for the dental implant shown in FIG. 1.

Referring initially to FIGS. 1-5 of the drawings, there is shown a biofunctional dental implant 1 which forms a first preferred embodiment of this invention. Dental implant 1 is suitable for use in the mouths of both humans and animals. The implant 1 includes a root portion 3 that is preferably manufactured from a biocompatible metallic (e.g., titanium or titanium alloy) or ceramic material that is adapted to be implanted and locked in the bone structure of a dental patient. The root portion 3 has a tapered implant casing 5 including a series of sharp edged barbs 7 extending around the exterior thereof and a set of screw threads 6 formed at the interior along a longitudinally extending channel 12. As is best shown in FIG. 1, the implant casing 5 of root portion 3 is installed within an implant socket that is made in the patient's bone structure so as to be able to support a crown portion (designated 40) above the gum line. The peripheral barbs 7 of implant casing 5 enable the root portion 3 of dental implant 1 to cut into the patient's bone structure during installation and then provide resistance against the root portion being accidentally pulled out of the implant socket. One or more anti-rotational notches 9 (best shown in FIGS. 2, 3 and 5) run axially along a side of the implant casing 5 to allow a subsequent growth of the patient's bone to mechanically lock and prevent a rotation of the root portion 3 following installation.

Vertical rows of radially extending channels and/or ports 10 are spaced around the implant casing 5. The longitudinally extending channel 12 through implant casing 5 communicates with the radially extending ports 10 and an axially aligned apical port 13. In this manner, human growth factor 14 can be delivered to and evenly distributed around the implant socket during installation so as to promote tissue growth over the root portion 3. In this same regard, the longitudinally extending channel 12 and the radially and axially extending ports 10 and 13 also cooperate to deliver to the implant socket an antibiotic (e.g., a bacteriacidal, such as chlorhexidine) or other fluids for the purposes of irrigation and aspiration and/or to treat bacterial lesions. By virtue of the foregoing, the necessity for a subsequent surgery might be avoided as a consequence of an otherwise untreated infection following installation of dental implant 1.

The top of the implant casing 5 of root portion 3 includes a flat head 16 that is located within the patient's bone structure so as to lie flush with the patient's gum line. A bevel 18 (best shown in FIGS. 2-4) is formed at opposite sides of the head 16 of the implant casing 5 in order to provide the root portion 3 with a scallop to better match the contour of and mate with the patient's surrounding tissue.

Projecting upwardly from the head 16 of implant casing 5 is a hollow cylindrical abutment 20. The cylindrical abutment 20 includes a plurality of (e.g., four) flexible splines 22 having a spring-like memory that are evenly spaced from one another. Each of the flexible splines 22 of abutment 20 has a sloping locking ridge 24 that runs vertically therealong. A set of locking grooves 26 extends circumferentially around the splines 22 of cylindrical abutment 20. The function of the locking ridges 24 and locking grooves 26 of abutment 20 will soon be explained.

Seated upon the flat head 16 of the root portion 3 of dental implant 1 is a cap 28 that is preferably manufactured from an elastomeric material. A (e.g., cylindrical) passage 30 runs longitudinally through the cap 28. A flexible sealing skirt 32 flares outwardly from the bottom of elastomeric cap 28. In the assembled configuration of the dental implant 1 shown in FIG. 1, with the cap 28 seated atop the flat head 28, the cylindrical abutment 20 is received through the cylindrical passage 30 formed in cap 28. The circumferentially extending locking grooves 26 around the splines 22 of abutment 20 will create a gripping surface with the cap 28 to prevent the inadvertent removal of cap 28 from the head 16 of root portion 3. Moreover, the flexible sealing skirt 32 of elastomeric cap 28 will be located at the junction of the root portion 3 and the soon to be described crown portion 40 so as to block the movement of fluids, food particles, and other possible contaminants towards the implant socket within which the dental implant 1 is anchored.

With the elastomeric cap 28 seated atop the flat head 16 of the implant casing 5, the crown portion 40 is positioned over cap 28. The crown 40 includes a hollow body that is preferably manufactured from a porcelain or metallic material. As is best shown in FIG. 1, the hollow crown portion 40 is provided with an internal liner, often referred to as a coping 42. The coping 42 is preferably manufactured from a ceramic or metallic material and is shaped to formed a close fit with the elastomeric cap 28 to lie thereunder. The crown portion 40 is typically cemented to the coping 42.

Each of the hollow crown portion 40 and the coping liner 42 are provided with a mounting opening 43 through which to receive the elastomeric cap 28 and an opposing installation opening 44 that is coaxially aligned with the mounting opening 43 and the cylindrical passage 30 through cap 28. To enable the combination crown portion 40 and coping 42 to be reliably connected to the root portion 3 in surrounding engagement with the elastomeric cap 28 atop the flat head 16 of implant casing 5, a rigid abutment screw 46 is provided. A series of screw threads 47 are located around one end of the abutment screw 46, and a relatively wide head 48 is formed at the opposite end. The head 48 of abutment screw 46 is provided with a (e.g., hex shaped) hole to receive a correspondingly shaped tool that is adapted to impart a rotational force to cause the abutment screw 48 to move inwardly of the implant casing 5 of the root portion 3 of dental implant 1.

During installation, one or more O-rings 50 are located within peripheral grooves 52 that are formed around the abutment screw 46. The threaded end 47 of abutment screw 46 is moved into a through hole 53 in a spline spreader 54 for receipt by the hollow abutment 20 of the implant casing 5 via the installation opening 44 in crown portion 40 and the cylindrical passage 30 in cap 28. The spline spreader 54 is provided with a number of (e.g., four) evenly spaced slots 56 that correspond to the number of flexible splines 22 of the abutment 20. The spline spreader 54 is dimensioned so as to fit between the flexible splines 22 of the abutment 20 (best shown in FIG. 1), whereby the vertical locking ridges 24 running along the sloping splines 22 are received by respective slots 56 in the spline spreader 54.

As the abutment screw 46 is tightened down against the root portion 3 and the screw threads 47 of abutment screw 46 are axially advanced past the abutment 20 and along the internal screw threads 6 of the longitudinally extending channel 20 of implant casing 5 (also best shown in FIG. 1), the spline spreader 54 carried by abutment screw 46 will ride over and apply a pushing force against the vertical locking rides 24 along the flexible splines 22 of abutment 20. The receipt of the spline spreader 54 by abutment 20 will cause the flexible splines 22 thereof to bend or rotate outwardly toward the elastomeric cap 28. Accordingly, the elastomeric cap 28 is compressed against the crown portion 40 and the coping 42 therewithin, whereby to hold the crown portion 40 against the root portion 3 of dental implant 1. Moreover, the elastomeric cap 28 will provide a resilient or cushion interface to minimize the transfer of shock between the crown and root portions 40 and 3 of dental implant 1.

Once the threaded abutment screw 46 has been fully inserted within the implant casing 5 of root portion 3 such that the screw threads 47 of abutment screw 46 are mated to the internal screw threads 6 along the channel 12 of implant casing 5, an additional holding force is provided by which to connect the crown portion 40 to the root portion 3. At this point, an optional filler (e.g., an elastomeric material, or the like) can be used to close the installation opening 44 formed in the crown portion 40 through which the abutment screw 46 is inserted for receipt by the root portion 3. By virtue of the foregoing, an integral biofunctional dental implant is provided for human and animal use which is relatively easy to manufacture and which will not become easily separated from the patient's bone structure during use.

Figure 6:
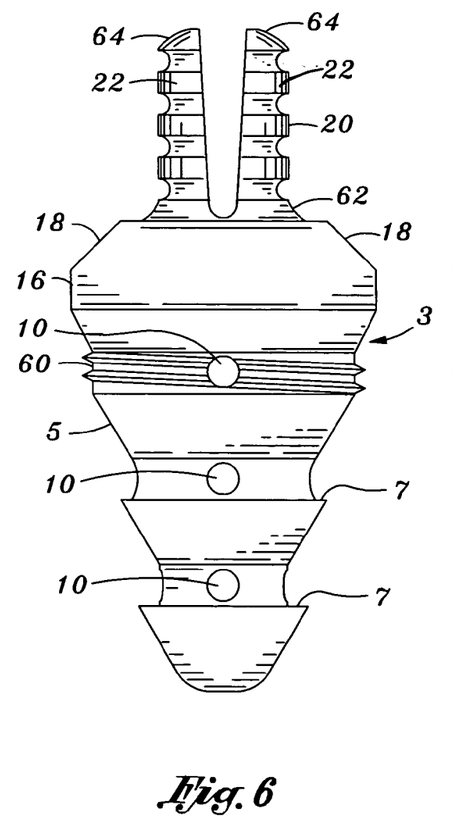
FIGS. 6 and 7 illustrate a modification of the root portion for the dental implant shown in FIG. 1.
Figure 7:
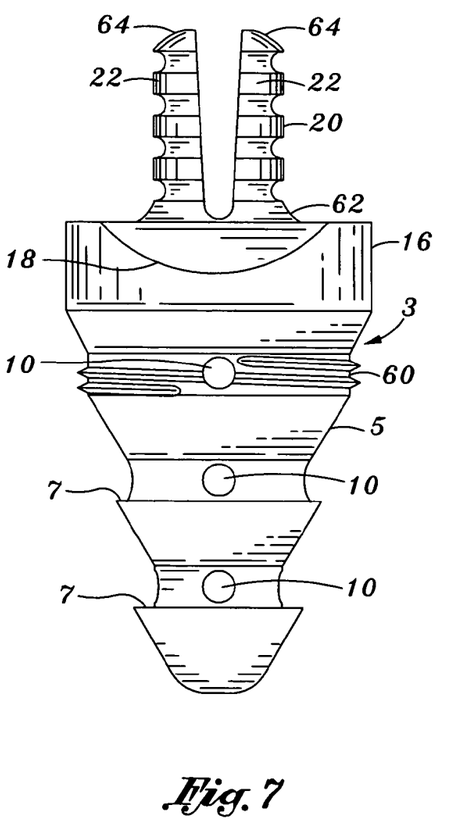

FIGS. 6 and 7 of the drawings show various modifications to the root portion 3 of the biofunctional dental implant 1 that was described while referring to FIGS. 1-5. As previously disclosed, the root portion 3 includes anti-rotational notches 9 that run axially along the implant casing 5 to prevent a rotation of the root portion following implantation of implant 1 in the patient's implant socket. The anti-rotational notches 9 can be replaced by or augmented with an optional set of sharp threads 60. The threads 60 extend around the implant casing 5 so as to coincide with the cortical portion of the patient's bone structure. The threads 60 cooperate with the barbs 7 of implant casing 5 to reliably anchor the root portion 3 within the bone structure so as to hold the root portion stationary following implantation.

In addition, the shape of the cylindrical abutment 20 may be changed to enhance the mating surface formed with the elastomeric cap 28 of FIGS. 1-5 that is to be seated on the flat head 16 of implant casing 5 in surrounding engagement with abutment 20. That is, the bottom of the abutment 20 is provided with an optional arcuate surface 62 to maximize the seal that is created by the receipt of the sealing skirt 32 of the cap 28 at the junction of the crown portion 40 and the root portion 3 in the manner shown in FIG. 1.

What is more, the square top of the cylindrical abutment 20 of FIGS. 1-5 is rounded in FIGS. 6 and 7. That is, each of the flexible splines 22 of abutment 20 is provided with an optional rounded tip 64, whereby to enhance the mating engagement of the elastomeric cap 28 around abutment 20.

Figure 8:
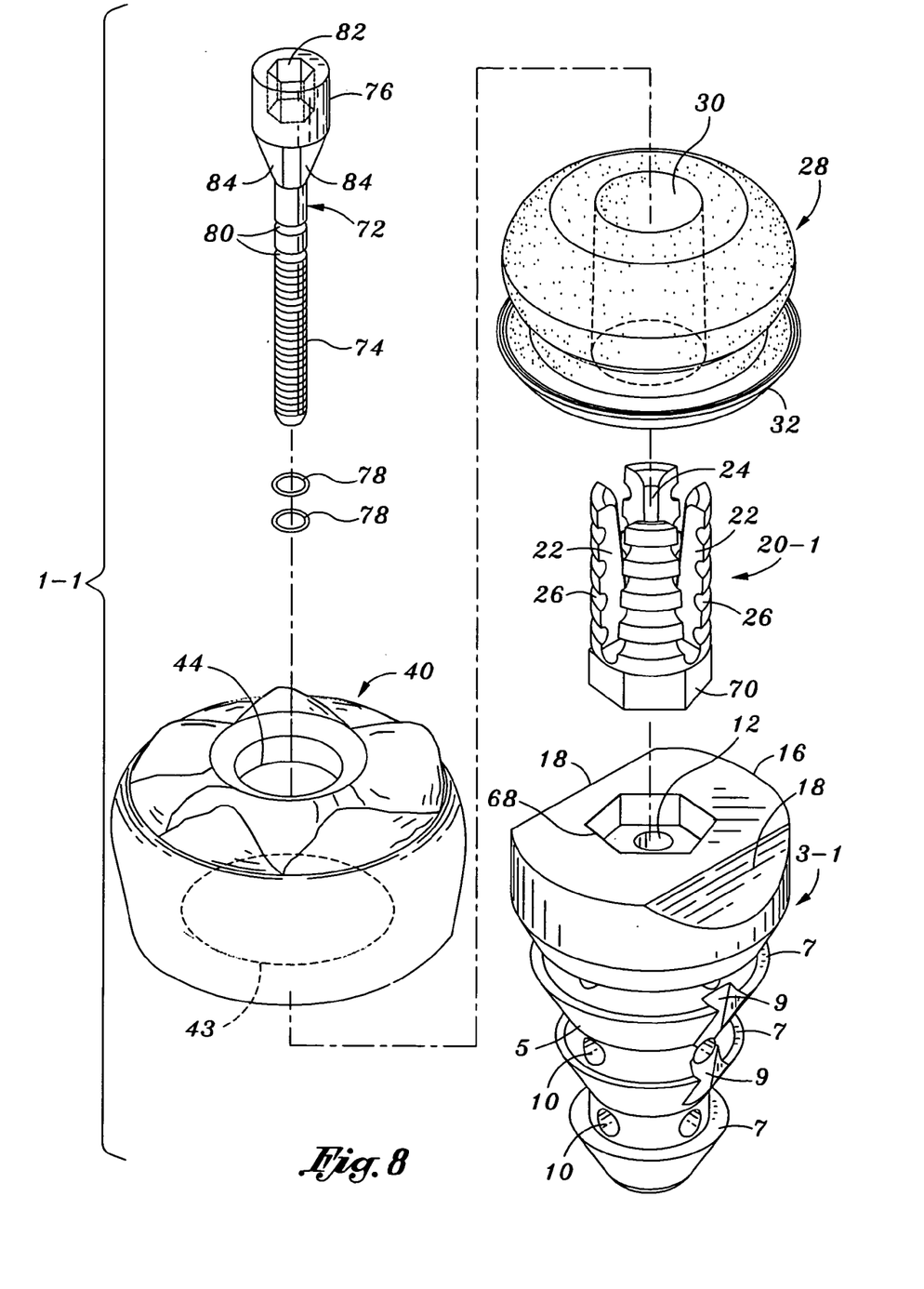
FIG. 8 is an exploded view showing a root portion and a crown portion to be detachably connected to one another to form a biofunctional dental implant according to another preferred embodiment.

FIG. 8 of the drawings shows other modifications to the dental implant 1 of FIGS. 1-5. The dental implant 1-1 of FIG. 8 includes a detachable cylindrical abutment 20-1 and eliminates the spline spreader (designated 54 in FIGS. 1-5). In particular, the one piece root portion 3 of FIGS. 1-5 is now replaced by the combination of a root portion 3-1 and a detachable abutment 20-1. The tapered implant casing 5, barbs 7, anti-rotational notches 9, human growth factor ports 10, flat head 16 and the bevels 18 formed therein are common to each of the root portion 3 and 3-1 of FIGS. 1-5 and 8 and, therefore, identical reference numerals had been used for each.

The implant casing 5 of root portion 3-1 is provided with a (e.g., hex shaped) mounting hole 68 formed at the top of the flat head 16. The mounting hole 68 is sized and shaped to accommodate a similar (e.g., hex shaped) base 70 of abutment 20-1. A plurality of (e.g., four) flexible splines 28 having a spring-like memory and respective sloping locking ridge 24 running vertically therealong project upwardly from base 70 at evenly spaced locations therearound. Locking grooves 26 are formed around the splines 22 so as to better grip the elastomeric cap 28 that is to be seated upon the flat head 16 of implantation 5 in surrounding engagement with the abutment 20-1.

The independent spline spreader 54 and the threaded abutment screw 46 of the dental implant 1 of FIGS. 1-5 are now replaced by a rigid, combined spline spreader and abutment screw 72. Like the abutment screw 46 earlier described, the combined spline spreader and screw 72 FIG. 8 has a series of screw threads 74 running around one end thereof and a relatively wide head 76 located at the opposite end. One or more O-rings 78 are located within peripheral grooves 80 formed around abutment screw 72.

The head 76 of the combined spline spreader and abutment screw 72 is provided with a (e.g. hex shaped) hole 82 to receive a correspondingly shaped tool that is adapted to impart a rotational force by which to cause the abutment screw 72 to move inwardly of the longitudinally extending channel 12 through the implant casing 5 of root portion 3-1. A plurality of angled flats 84 extend downwardly from the head 76 of the combined spline spreader and abutment screw 72 to form a tapered area. The number (e.g. four) of flats 84 carried by abutment screw 72 correspond to the number of flexible splines 22 of the abutment 20-1. The flats 84 extend from head 76 at an angle so as to match the angle of the sloping locking ridges 24 that run vertically along the splines 22 of abutment 20-1. The head 76 is dimensioned to fit between the flexible splines 22 of the abutment 20-1, whereby the vertical locking ridges 24 of the splines 22 are received against respective flats 84 of the combined spline spreader and abutment screw 72.

During installation, once the root portion 3-1 has been implanted in the patient's bone structure, the base 70 of abutment 20-1 is received within the correspondingly shaped mounting hole 68 in the flat head 16 of implant casing 5. The elastomeric cap 28 is seated atop the flat head 16 in surrounding engagement with the upstanding abutment 20-1. The crown portion 40 and the coping liner thereof (not shown) are positioned over the cap 28 by way of mounting opening 43. The threaded end 74 of the combined spline spreader and abutment screw 72 is then inserted into the longitudinally extending channel 12 of implant casing 5 via the axial alignment of the installation opening 44 of crown portion 40, the cylindrical passage 30 through elastomeric cap 28, and the abutment 20-1.

As the combined spline spread and abutment screw 72 is tightened down against the root portion 3-1 and the screw threads 74 of abutment screw 72 are advanced past the abutment 20-1 and along the internal screw threads (designated 6 FIG. 3) of the longitudinally extending channel 20 of implant casing 5, the angled flats 84 that are carried by abutment screw 72 will ride over the sloping ridges 24 and apply a pushing force against the flexible splines 22 of abutment 20-1. The receipt of the flats 84 against the sloping ridges 24 will cause the flexible splines 22 to bend or rotate outwardly towards the elastomeric cap 28, whereby the cap is compressed against the crown portion 40 so as to hold the crown portion 40 against the root portion 3-1 of dental implant 1-1. The fully inserted combined spline spreader and abutment screw 72 provides a hold-down force by which to connect the flexible abutment 20-1 to the root portion 3-1.

Because the abutment 20-1 is detachably connected to the implant casing 5 of root portion 3-1, a defective or broken abutment can be replaced, whenever necessary, without requiring a new surgery. The one piece combined spline spreader and abutment screw 72 eliminates the addition of the spline spreader 54 of FIG. 1-5 and thereby makes the dental implant 1-1 of FIG. 8 more efficient and inexpensive to manufacture.

Figure 9:
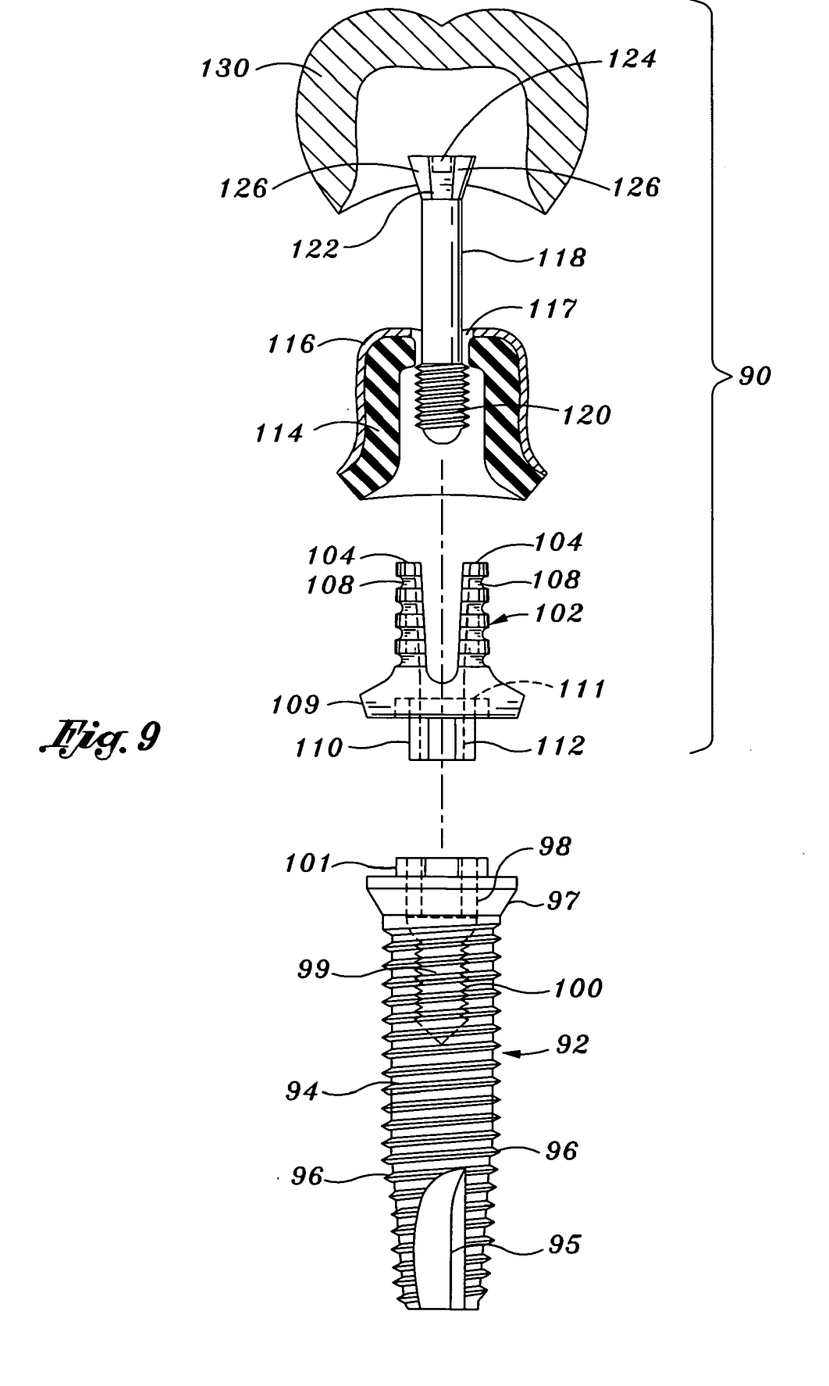
FIG. 9 is an exploded view showing a replaceable crown portion to be detachably connected to an existing root portion to form a biofunctional dental implant according to yet another preferred embodiment.
Figure 10:
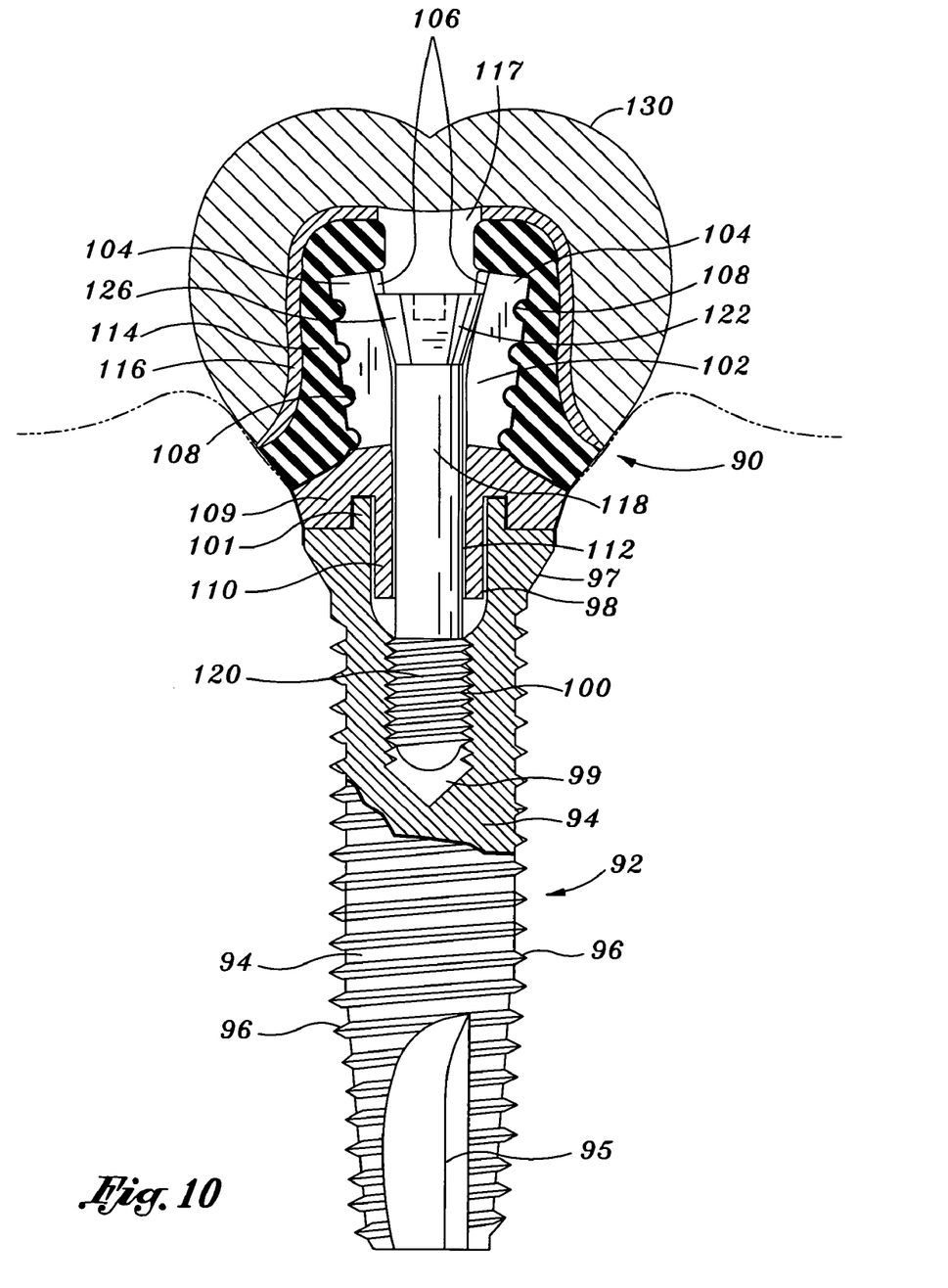
FIG. 10 shows the replaceable crown portion of the dental implant of FIG. 9 detachably connected to the existing root portion.

FIGS. 9 and 10 of the drawings show a replacement crown assembly 90 for a conventional dental implant (commonly known as a Thommen Medical implant) according to another preferred embodiment of this invention. The dental implants 1 and 1-1 of FIGS. 1-8 first require the installation of a root portion within an implant socket formed in the patient's bone structure so that a crown portion can be later connected to the root portion. In the case of FIGS. 9 and 10, should an existing crown portion be subjected to breakage or failure, it can be disconnected from the existing root portion 92 and removed from the patient's mouth. The replacement crown assembly 90 of FIGS. 9 and 10 may then be quickly and easily substituted for the defective crown portion without requiring a new surgery.

The root portion 92 to which the replacement crown assembly 90 is to be connected is conventional and is of the kind that is typically installed in the patient's bone structure during dental surgery. Briefly, the existing root portion 92 includes a generally cylindrical implant housing 94 that is manufactured from metal or ceramic and includes a longitudinally extending anti-rotational slot 95 and a set of sharp threads 96 extending circumferentially therearound to cut into the bone structure and anchor the root portion in place. The existing root portion 92 includes a relatively wide head 97 that is located at one end of the implant housing 94. A female hex shaped opening 98 is formed in the head 97. The female opening 98 in head 97 communicates with a channel 99 that runs longitudinally through the interior of implant housing 94. The longitudinally running channel 99 of the existing root portion 92 is provided with a set of internal screw threads 100 to which the replacement crown portion 90 is mated in a manner that will now be described.

The replacement crown portion 90 includes a hollow cylindrical abutment 102 which is similar in function to the abutments 20 and 20-1 of FIGS. 1-8. That is, the abutment 102 of FIGS. 9 and 10 includes a plurality of flexible splines 104 having a spring-like memory and respective sloping locking ridges 106 (as shown in FIG. 10) running vertically therealong. Locking grooves 108 are formed around the splines 104 by which to improve the grip of an elastomeric cap 114. Abutment 102 includes a relatively wide base 109 that is sized to match the opposing head 97 on top of the implant casing 94 of existing root portion 92. A male (e.g. hex shaped) fitting 110 projects downwardly from a cavity 111 formed in the base 109 of abutment 102. The male fitting 110 is shaped so as to be received, during installation, within the corresponding female opening 98 that is formed in a rise 101 that projects upwardly from the head 97 atop implant housing 94. A passage 112 extends longitudinally through the base 109 of the male fitting 110 of abutment 102 to be axially aligned with the longitudinally extending channel 99 through implant housing 94.

The elastomeric cap 114 is dimensioned so as to be seated upon the base 109 of abutment 102 to lie in surrounding engagement with the flexible splines 104 thereof. A metallic, ceramic or plastic coping 116 is positioned over abutment 102. Each of the elastomeric cap 114 and the coping 116 thereover is provided with an installation opening 117 through which to receive an abutment screw 118.

The abutment screw 118 is similar in function to the combined spline spreader and abutment screw 72 that was previously described while referring to FIG. 8. That is, the abutment screw 118 has a series of screw threads 120 running around one end thereof and a tapered head 122 located at the opposite end. The tapered head 122 of abutment screw 118 is provided with a (e.g. hex shaped) hole 124 to receive a correspondingly shaped tool that is adapted to impart a rotational force to cause the abutment screw 118 to move inwardly of the threaded channel 99 that runs longitudinally through the implant housing 94 of the existing root portion 92. A plurality of angled flats 126 extend downwardly along the tapered head 122 of abutment screw 118. The number of flats 126 carried by the tapered head 122 of abutment screw 118 corresponds to the number of flexible splines 108 of abutment 102. The tapered head 122 of the abutment screw 118 is dimensioned to fit between the flexible splines 104 of abutment 102, whereby the vertical locking ridges 106 of the splines 108 are received against respective flats 126 of the tapered head 122.

Once an existing crown portion has been removed from the existing root portion 92 to be replaced by the crown portion 90 of FIGS. 9 and 10, the abutment 102 is mounted on top of root portion 92, such that the base 109 of abutment 102 is seated on the opposing head 97 of root portion 93, the rise 101 projecting from the head 97 of root portion 92 is received within the cavity 111 formed in the base 109 of abutment 102 and the male fitting 110 of abutment 102 is received within the female opening 98 formed in the head 97. The elastomeric cap 114 and the coping liner 116 thereover are positioned against the base 109 of abutment 102 to lie in surrounding engagement with the flexible splines 104 thereof (best shown in FIG. 10). As is also best shown in FIG. 10, the threaded end 120 of the abutment screw 118 is now inserted into the threaded channel 99 of implant housing 94 via the axially alignment of the installation opening 117 through elastomeric cap 114 and the passage 112 through abutment 102.

As the abutment screw 118 is tightened against the existing root portion 92 and the screw threads 120 of abutment screw 118 are mated to the internal screw threads 100 along the longitudinally extending channel 99 through implant housing 94, the angled flats 126 carried by the tapered head 122 of abutment screw 118 will ride over the sloping ridges 106 and apply a pushing force against the flexible splines 104 of abutment 102. The receipt of the flats 126 against ridges 106 will cause the flexible splines 104 to bend or rotate outwardly towards the elastomeric cap 114, whereby the cap will be compressed once the crown 130 is attached. The fully inserted abutment screw 118 provides sufficient hold-down force to connect the elastomeric cap 114 and the abutment 102 to the existing root portion. The crown 130 is then cemented over top the coping liner 116 to complete the replacement crown portion 90. However, prior to attachment of the crown 130, the installation opening 117 through the cap 114 and coping liner 116 may be filled with a suitable (e.g. elastomeric) filler.

Figures 11, 12:
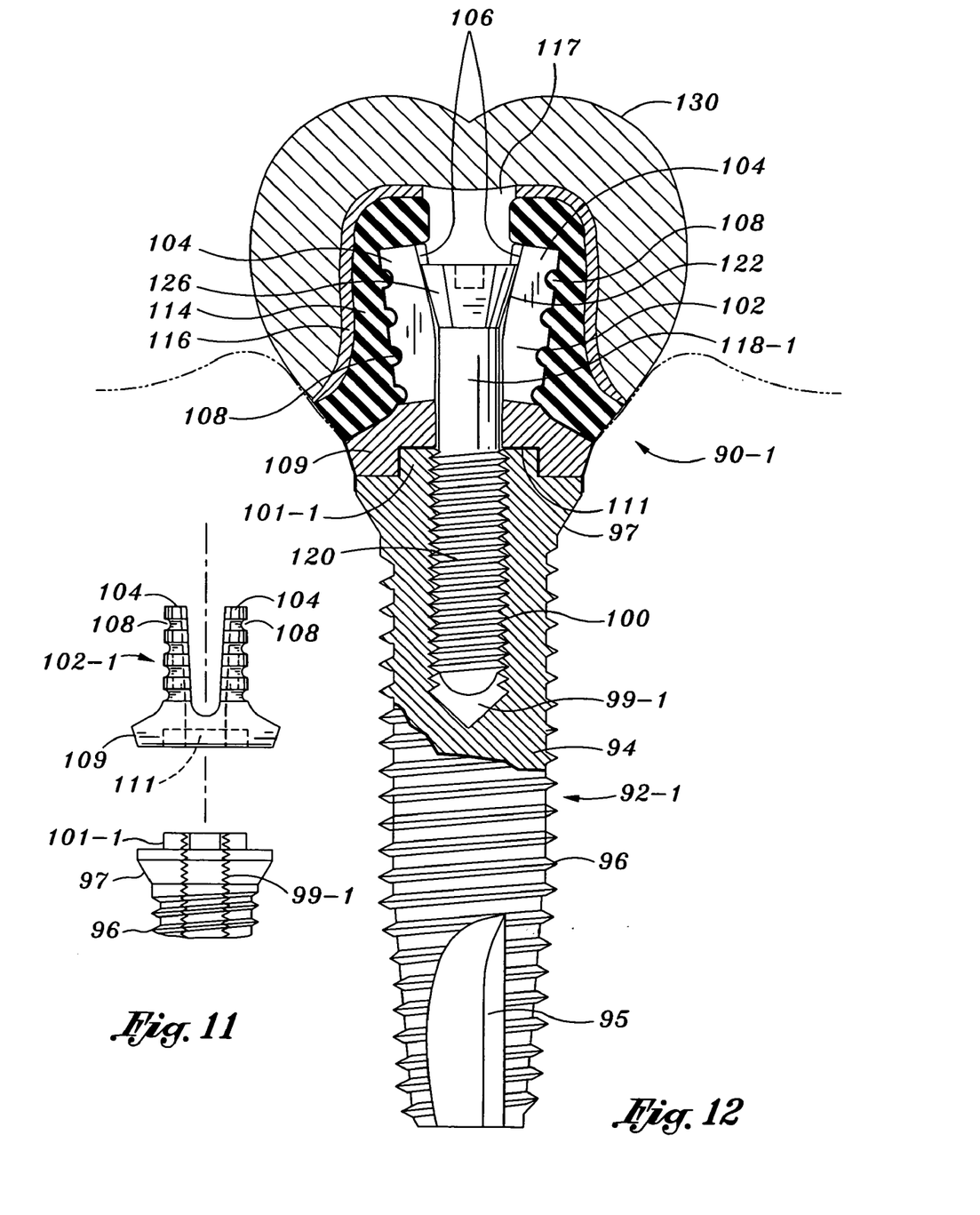
FIG. 11 is a cross-section showing a replaceable crown portion and an existing root portion detachably connected to one another to form a biofunctional dental implant according to a further preferred embodiment.
FIG. 12 shows a detail to illustrate the detachable connection of the replaceable crown portion of the dental implant of FIG. 11 to the existing root portion.

FIGS. 11 and 12 of the drawings show another conventional dental implant (commonly known as a Branemark implant) having a modified crown portion to be used in substitution of the replacement crown portion 90 of FIGS. 9 and 10. In the replacement crown portion 90, a male fitting 110 which depends downwardly from a cavity 111 formed in the base 109 of the abutment 102 is received within a female opening 98 that is formed in the head 97 of the existing root portion 92-1 and a rise 101 projecting upwardly from the head 97 of root portion 92 is received within the cavity 111, whereby the abutment 102 is detachably connected to the root portion 92-1. In the case of the replacement crown portion 90-1 of FIGS. 11 and 12, the former male fitting 110 is removed from the cavity 111 formed in the relatively wide base 109 of the cylindrical abutment 102-1. The abutment 102-1 is detachably connected to the existing root portion 92-1 when the rise 101-1 which projects upwardly from the head 97 of root portion 92 is received within the cavity 111 formed in the base 109 of abutment 102-1, such that the base 109 of abutment 102-1 and the head 97 of root portion 92-1 are disposed face-to-face one another. The remaining reference numerals used in FIGS. 9 and 10 are also used in FIGS. 11 and 12 to designate identical parts.

The modified crown portion 90-1 of FIGS. 11 and 12 is used as a replacement for a broken or defective crown that is removed from an existing root portion 92-1 of the type having a relatively long threaded channel 99-1 running longitudinally through the implant housing 94 in substitution of the female opening (designated 98 in FIGS. 9 and 10). In this same regard, the abutment screw 118-1 has a relatively long threaded end 120 to be mated to the internal screw threads 100 that run along the channel 99-1.

Figures 13, 14:
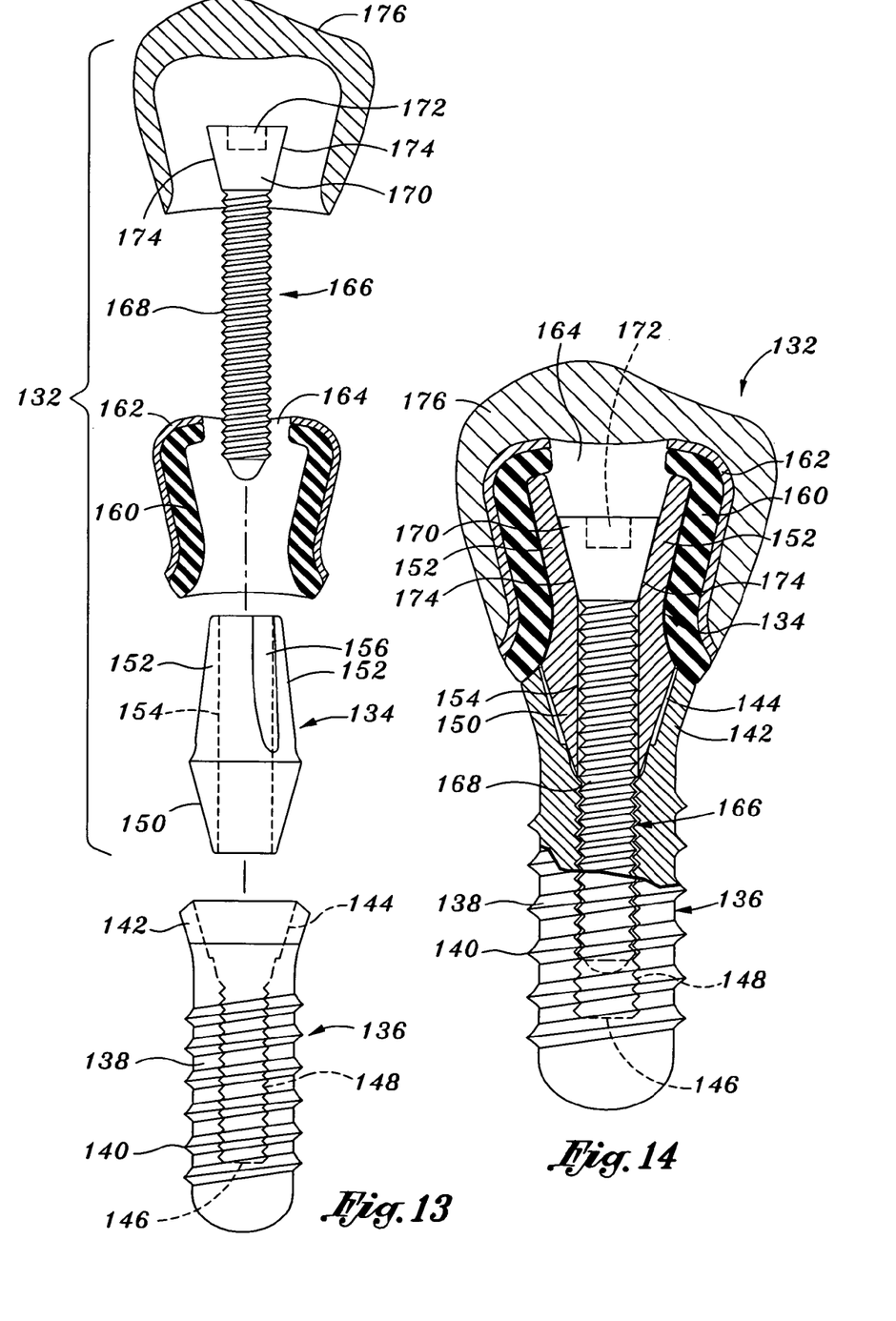
FIG. 13 is an exploded view showing a replacement crown portion to be detachably connected to an existing root portion to form a biofunctional dental implant according to a still further preferred embodiment.
FIG. 14 is a cross-section showing the replaceable crown portion of the dental implant of FIG. 13 detachably connected to the existing root portion.

FIGS. 13 and 14 of the drawings show a modified crown portion 132 and a modified cylindrical abutment 134 to be attached to an existing root portion 136 of a conventional dental implant commonly known as an ITI/Straumann implant. Briefly, the existing root portion 136 is of the type having a tubular implant housing 138 and a set of sharp screw threads 140 extending circumferentially therearound to anchor the root portion 136 within an implant socket in the patient's bone structure. A flared head 142 is located at the top of implant housing 138. A correspondingly flared access opening 144 is formed in the head 142 of implant housing 138. The access opening 144 communicates with a channel 146 that runs longitudinally through the implant housing 138. A set of internal screw threads 148 extends along the longitudinal channel 146.

Unlike the generally cylindrical abutments described above, the modified abutment of crown portion 134 of FIGS. 13 and 14 includes a tapered lower section 150 that is shaped to be received within the access opening 144 in the flared head 142 of the existing root portion 136 (best shown in FIG. 14). A pair of flexible splines 152 having a spring-like memory project upwardly from the lower section 150 of abutment 134. A cylindrical channel 154 runs between the splines 152 and through the lower section 150 of abutment 134 so as to lie in axial alignment with the threaded channel 146 through the implant housing 138 of root portion 136. An anti-rotational slot 156 is formed in one of the splines 152 for a purpose that will soon be described.

An elastomeric cap 160 is dimensioned so as to be seated upon the flared head 142 of the root portion 136 and lie in surrounding engagement with the flexible splines 152 of abutment 134 (also best shown in FIG. 14). A metallic, ceramic or plastic coping 162 is positioned over cap 160. Each of the elastomeric cap 160 and the coping 162 thereover is provided with an installation opening 164 through which to receive an abutment screw 166.

The abutment screw 166 is similar in function to the combined spline spreader and abutment screw that has been earlier disclosed. In particular, the abutment screw 166 has a series of screw threads 168 running around one end thereof and a tapered head 170 located at the opposite end. The tapered head 170 of abutment screw 166 is provided with a (e.g., hex shaped) hole 172 to receive a correspondingly shaped tool that is adapted to impart a rotational force to cause the abutment screw 166 to move inwardly of the threaded channel 146 that runs longitudinally through the implant housing 138 of the existing root portion 136. The tapered head 170 of abutment screw 166 carries a pair of oppositely aligned flats 174. The tapered head 170 of screw 166 is dimensioned to fit between the pair of flexible splines 152 of abutment 134, whereby the splines 152 are received against respective flats 174 carried by the tapered head 170.

In the assembled configuration of FIG. 14, the abutment 134 is mounted on top of the existing root portion 136 such that the tapered lower section 150 of abutment 134 is received within the correspondingly shaped access opening 144 that is formed in the flared head 142 atop the implant housing 138. The elastomeric cap 160 and the coping liner 162 thereover are positioned against the abutment 134 so as to be seated against the flared head 142 of the existing root portion 136 and lie in surrounding engagement with the flexible splines 152 of abutment 134. The anti-rotational slot (designated 156 in FIG. 13) locks the abutment 134 to cap 160. The threaded end 168 of the abutment screw 166 is now inserted into the threaded channel 146 of implant housing 138 via the axial alignment of the installation opening 164 through the elastomeric cap 160 and the cylindrical channel 154 through abutment 134.

As the abutment screw 166 is tightened against the existing root portion 136 and the screw threads 168 of abutment screw 166 are mated to the internal screw threads 148 along the longitudinally extending channel 146 through implant housing 138, the flats 174 carried by the tapered head 170 of abutment screw 166 will ride over and apply a pushing force against the flexible splines 152 of abutment 134. The receipt of the flats 174 will cause the flexible splines 152 to bend or rotate outwardly towards the elastomeric cap 160 whereby the cap will be compressed once the crown 176 is installed. The fully inserted abutment screw 166 provides sufficient hold-down force to connect the elastomeric cap 160 and the abutment 134 to the existing root portion 136. The crown 176 is then cemented over top the coping liner 162 to complete the crown portion 132. However, prior to attachment of the crown 176, the installation opening 164 through the cap 160 and coping liner 162 may be filled with a suitable (e.g. elastomeric) filler.

Figures 15, 16:
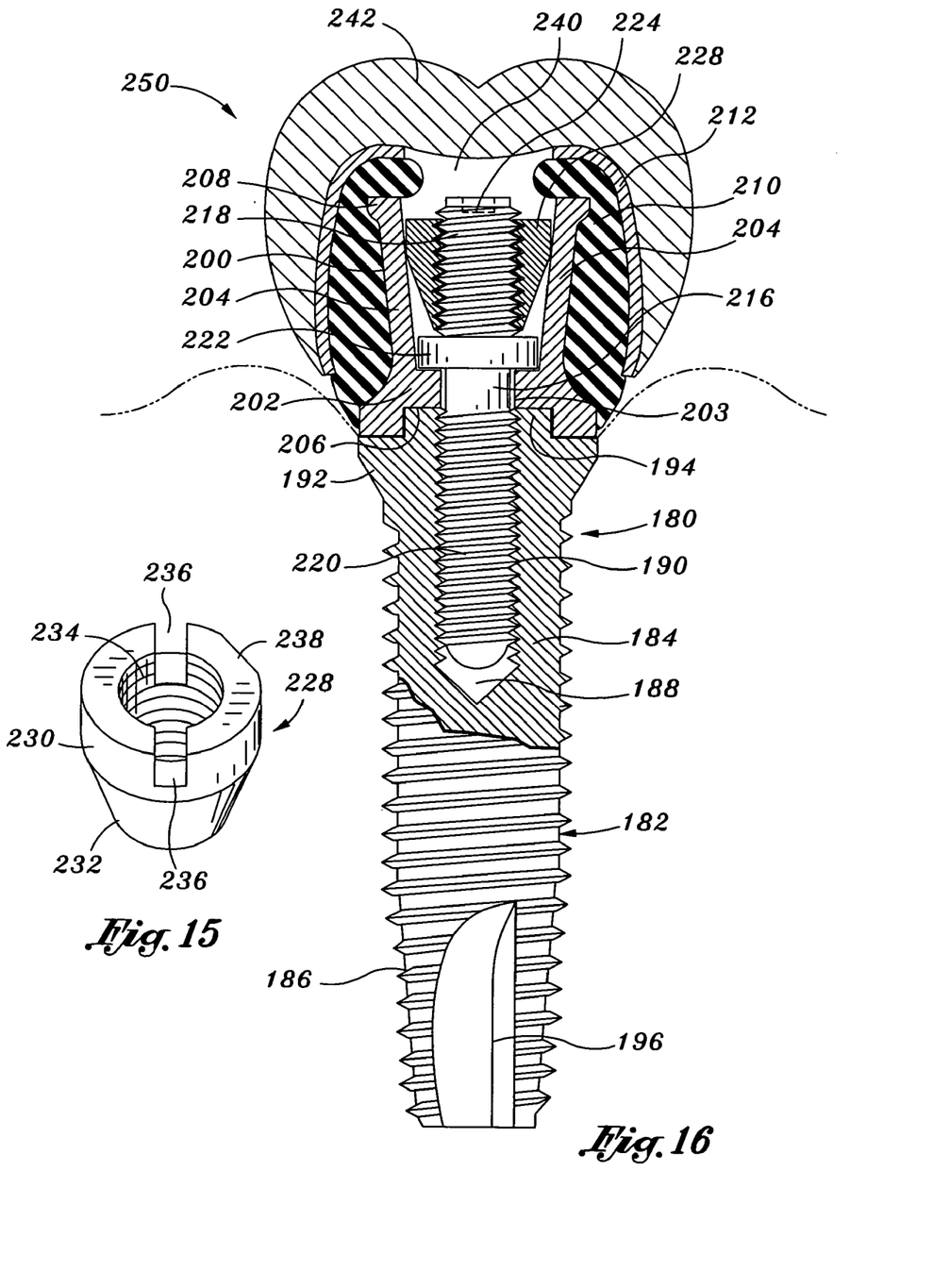
FIG. 15 shows a replaceable crown portion having a locking nut by which the crown portion is detachably connected to an existing root portion of the type shown in FIG. 11.
FIG. 16 shows details of the locking nut of FIG. 15.

FIGS. 15 and 16 of the drawings show a dental implant 180 including a modified cylindrical abutment 200, a correspondingly modified one piece abutment screw 216, and a locking nut 228 to facilitate the repair or replacement of a broken or worn crown. The dental implant 180 includes an existing root portion 182 of the Branemark type that was previously shown and described while referring to FIG. 11. Briefly, the root portion 182 of dental implant 180 has a tubular implant housing 184 and a set of sharp screw threads 186 extending circumferentially therearound to anchor the root portion 182 within an implant socket formed in the patient's bone structure. A relatively long threaded channel 188 having screw threads 190 runs longitudinally through the implant housing 184. The root portion 182 includes a tapered head 192 having a rise 194 projecting upwardly therefrom. An anti-rotational slot 196 is formed in the implant housing 184 to prevent a rotation of root portion 182 following implantation.

The modified abutment 200 of the crown portion 250 of dental implant 180 has a wide base 202, a passageway 203 extending longitudinally through the base 202, and a plurality of smooth flexible splines 204 projecting upwardly from base 202. A cavity 206 is formed in the bottom of the base 202 to receive the rise 194 which projects upwardly from the head 192 of root portion 182 to complete the assembled dental implant 180 as shown in FIG. 16. Each of the plurality of flexible splines 204 of abutment 200 slopes outwardly from the base 202 thereof. A locking tip 208 projects outwardly from the top of each flexible spline 204.

The crown portion 250 of dental implant 180 also includes an elastomeric cap 210 which is covered by a coping 212 that is preferably manufactured from metal, plastic, ceramic, or the like. In the assembled dental implant configuration of FIG. 16, the combination elastomeric cap 210 and the coping 212 surround the abutment 200 to absorb shock that is transmitted to the crown portion 250. The locking tips 208 of the flexible splines 204 of the abutment 200 press into the elastomeric cap 210.

The modified one piece abutment screw 216 of dental implant 180 includes an upper set of screw threads 218 and a lower set of screw threads 220. Located between the upper and lower sets of screw threads 218 and 220 of abutment screw 216 is a relatively wide integral locking washer 222. A (e.g., hex) opening 224 is formed in the top of abutment screw 216 to receive a suitable tool by which to impart a rotational force to screw 216 during installation.

The (e.g., stainless steel) locking nut 228 of dental implant 180 (best shown in FIG. 15) includes a ring-like nut body 230 that narrows to a tapered conical bottom 232. A set of internal screw threads 234 runs around the body 230 and the tapered bottom 232 of locking nut 228. A pair of opposing installation slots 236 are formed through the body 230 of locking nut 228 to receive a suitable tool by which to impart a rotational force to nut 228 during installation. One or more flats 238 are formed in the body 230 of locking nut 228 for a purpose that will soon be described.

During installation, the replacement crown portion 250 is laid atop the existing root portion 182 such that the rise 194 which projects upwardly from the head 192 of implant casing 182 is received in the cavity 206 formed in the base 202 of the abutment 200. The abutment screw 216 is inserted through an installation opening 240 in the crown portion 250 to be removably connected to the root portion 182. That is, a rotational force is applied to the abutment screw 216 at the hex opening 224 thereof so that the lower set of screw threads 220 is axially advanced through the passageway 203 in the base 202 of abutment 200 and into mating engagement with the screw threads 190 that run around the longitudinally extending channel 188 through implant housing 184. The axial movement of abutment screw 216 into the root portion 182 continues until the wide integral locking washer 222 of abutment screw 216 is seated upon the base 202 of abutment 200. At this point, the upper set of screw threads 218 of abutment screw 216 stands upwardly from the washer 222 to be surrounded by the flexible splines 204 of abutment 200.

It may be appreciated that with the locking washer 222 seated upon the base 202 of abutment 200, the abutment screw 216 will be stabilized in the dental implant 180 and coaxially aligned with the abutment 200 to receive the locking nut 228. That is, locking washer 222 provides a broad surface by which to prevent the abutment screw 216 from tipping towards one of the flexible splines 204 of abutment 200.

Next, the locking nut 228 is coupled to the abutment screw 216 through the installation opening 240 in crown portion 250. A rotational force is applied to the locking nut 228 at the installation slots 236 thereof (best shown in FIG. 15) so that the internal screw threads 234 of locking nut 228 are axially advanced into mating engagement with the upper set of screw threads 218 of abutment screw 216. As the locking nut 228 is rotated around the abutment screw 216, the ring-like nut body 230 will ride over and apply a pushing force against the outwardly sloping flexible splines 204 of abutment 200. In this regard, the spacing between opposing flexible splines 204 must be sufficient to accommodate the sliding movement of the nut body 230 therebetween.

The receipt of the body 230 of locking nut 228 within abutment 200 will cause the flexible splines 204 to bend and rotate outwardly towards the elastomeric cap 210 whereby the cap will be compressed against the coping 212 lying thereover. The flat 238 (also best shown in FIG. 15) that is formed in the nut body 230 holds the locking nut 228 in place against the abutment 200 so as to prevent loosening. The axial movement of locking nut 228 along the upper set of screw threads 218 of abutment screw 216 continues until the tapered bottom 232 of nut 228 is seated against the locking washer 222 of abutment screw 216.

The locking nut 228 is tightened down against the locking washer 222 to provide sufficient hold down force to detachably connect the abutment 200 and the elastomeric cap 210 of replacement crown portion 250 to the existing root portion 180. The installation opening 240 through crown portion 250 is first filled with a suitable (e.g., elastomeric) filler and the crown 242 is then cemented over the coping 212 to complete the replacement crown portion 250 and the installation of the dental implant 180.

In each of the dental implant embodiments described when referring to FIGS. 1-16, an abutment post or screw is used to connect a crown portion to a root portion. In this regard, the force generated for holding the crown portion atop the root portion can be selectively adjusted to enable the crown portion to move or slide relative to the root portion and thereby better emulate the function of a natural tooth for enhanced mastication.

The invention claimed is:

1. A dental implant for affixing a crown portion to a bone structure in the mouth of a patient, said dental implant comprising:
   a root portion to be implanted below the patient's gum line within an implant socket in the patient's bone structure, said root portion having a channel extending longitudinally therethrough;
   a flexible abutment projecting upwardly from said root portion, said flexible abutment having a plurality of flexible splines and a passageway extending longitudinally therethrough and being axially aligned with the channel extending longitudinally through said root portion;
   a crown portion including an elastomeric cap to surround said flexible abutment and a crown to surround said elastomeric cap; and
   an abutment post moving through said crown portion and into receipt by the axially aligned channel extending longitudinally through said root portion and the passageway extending longitudinally through said flexible abutment, said abutment post applying an outward pushing force against said flexible abutment by which to cause the plurality of flexible splines thereof to rotate towards and compress said elastomeric cap against said crown, whereby to hold said flexible abutment against the crown portion and thereby attach said crown portion to said root portion.

2. The dental implant recited in claim 1, further comprising a spline spreader located between the plurality of flexible splines of said flexible abutment, the movement of said abutment post through said crown portion forcing said spline spreader to slide along said plurality of flexible splines by which to generate said outward pushing force for causing said flexible splines to rotate towards and compress said elastomeric cap against said crown.

3. The dental implant recited in claim 2, wherein said abutment post has a relatively wide head at one end thereof, and each of said plurality of flexible splines of said flexible abutment has a sloping ridge running therealong, said relatively wide head of said abutment post forcing said spline spreader to ride over the sloping ridges of said plurality of flexible splines as said abutment post moves through said crown portion by which to generate said output pushing force against said flexible abutment.

4. The dental implant recited in claim 3, wherein said spline spreader has a hole extending therethrough and a plurality of slots located therearound, said abutment post moving through each of said crown portion and the hole through said spline spreader, such that the relatively wide head of said abutment post moves into engagement with said spline spreader for forcing said spline spreader to slide along the sloping ridges of said plurality of splines with each of said plurality of splines being received within a respective one of said plurality of slots.

5. The dental implant recited in claim 1, wherein said root portion includes a plurality of radially extending ports communicating with said longitudinally extending channel so that at least one of a human growth factor and an antibiotic can be delivered to the implant socket prior to said abutment posts moving through said crown portion and into receipt by said longitudinally extending channel.

6. The dental implant recited in claim 1, wherein said root portion has at least one bevel formed therein so as to be located at the gum line of the patient when said root portion is implanted within the implant socket.

7. The dental implant recited in claim 1, wherein said root portion has a series of screw threads extending therearound and a plurality of sharp barbs projecting outwardly therefrom, said screw threads and said barbs cutting into the patient's bone structure to anchor said root portion at the implant socket within which said root portion is implanted.

8. The dental implant recited in claim 1, wherein said root portion has at least one anti-rotational notch formed therein to engage the patient's bone structure and prevent a rotation of said root portion relative to the implant socket within which said root portion is implanted.

9. A dental implant for affixing a crown portion to the bone structure in the mouth of a patient, said dental implant comprising:
   a root portion to be implanted below the patient's gum line within an implant socket in the patient's bone structure, said root portion having a channel extending longitudinally therethrough;
   a flexible abutment detachably connected to and projecting upwardly from said root portion such that at least some of said flexible abutment is removably received within the longitudinally extending channel through said root portion, said flexible abutment having a passageway extending longitudinally therethrough and being axially aligned with the channel extending longitudinally through said root portion;
   a crown portion surrounding said flexible abutment; and
   an abutment post moving through said crown portion and into receipt by the axially aligned channel extending longitudinally through said root portion and the passageway extending longitudinally through said flexible abutment by which to detachably connect said flexible abutment to said root portion within said longitudinally extending channel thereof, said abutment post applying an outward pushing force against said flexible abutment by which to hold said flexible abutment against said crown portion and thereby attach said crown portion to said root portion.

10. The dental implant recited in claim 9, wherein said crown portion includes an elastomeric cap to surround said flexible abutment and a crown to surround said elastomeric cap, the outward pushing force applied against said flexible abutment by said abutment post causing said flexible abutment to compress said elastomeric cap against said crown.

11. The dental implant recited in claim 10, wherein said flexible abutment includes a plurality of flexible splines, the outward pushing force applied against said flexible abutment by said abutment post causing said flexible splines to rotate towards and compress said elastomeric cap against said crown.

12. The dental implant recited in claim 11, wherein said abutment post has a relatively wide head at one end thereof, and each of said plurality of flexible splines of said flexible abutment has a sloping ridge running therealong, the relatively wide head of said abutment post riding over the sloping ridges of said plurality of flexible splines as said abutment post moves through said crown portion by which to generate said outward pushing force against said flexible abutment for causing said flexible splines to rotate towards and compress said elastomeric cap against said crown.

13. The dental implant recited in claim 11, wherein the relatively wide head of said abutment post includes a tapered area that slides over the sloping ridges of said plurality of splines as said abutment post moves through said crown portion by which to generate said outward pushing force against said flexible abutment for causing said flexible splines to rotate towards and compress said elastomeric cap against said crown.

14. The dental implant recited in claim 9, wherein said root portion has at least one anti-rotational notch formed therein and at least one sharp barb projecting outwardly therefrom, said anti-rotational notch and said sharp barb engaging the patient's bone structure to prevent a rotation and the removal of said root portion relative to the implant socket within which said root portion is implanted.

15. A replacement crown assembly to be removably connected to an existing root portion that is implanted below a patient's gum line to complete a dental implant, said replacement crown assembly comprising:
    a flexible abutment to be connected to the existing root portion so as to project upwardly therefrom, said root portion having a screw threaded channel extending longitudinally therethrough and said flexible abutment having a passageway extending longitudinally therethrough and being axially aligned with the screw threaded channel through said root portion;
    an elastomeric cap surrounding said flexible abutment;
    a crown surrounding said elastomeric cap; and
    a removable abutment post having a screw threaded end rotated in a first direction through said elastomeric cap and the longitudinally extending passage of said flexible abutment for receipt by the screw threaded channel of said existing root portion by which to detachably connect said flexible abutment to said existing root portion, said abutment post applying an outward pushing force against said flexible abutment by which to cause said elastomeric cap to be compressed against said crown, the screw threaded end of said removable abutment post being rotated in an opposite direction out of said root portion and away from said flexible abutment by which said flexible abutment is disconnected from said existing root portion.

16. The replacement crown assembly recited in claim 15, wherein said flexible abutment includes a plurality of flexible splines, the outward pushing force applied against said flexible abutment by said abutment post causing said flexible splines to rotate towards and compress said elastomeric cap against said crown.

17. The replacement crown assembly recited in claim 16, wherein said abutment post has a relatively wide head at one end thereof, and each of said plurality of flexible splines of said flexible abutment has a sloping ridge running therealong, the relatively wide head of said abutment post riding over the sloping ridges of said plurality of flexible splines as said abutment post moves through the longitudinally extending passage of said flexible abutment by which to generate said outward pushing force against said flexible abutment for causing said flexible splines to rotate towards and compress said elastomeric cap against said crown.

18. The replacement crown assembly recited in claim 17, wherein the relatively wide head of said abutment post includes a tapered area that slides over the sloping ridges of said plurality of splines as said abutment post moves through the longitudinally extending passage of said flexible abutment by which to generate said outward pushing force against said flexible abutment for causing said flexible splines to rotate towards and compress said elastomeric cap against said crown.

19. A replacement crown assembly to be removably connected to an existing root portion that is implanted below a patient's gum line to complete a dental implant, said replacement crown assembly comprising:
    a flexible abutment to be connected to the existing root portion so as to project upwardly therefrom, said flexible abutment having a passageway extending longitudinally therethrough;
    an elastomeric cap surrounding said flexible abutment;
    a crown surrounding said elastomeric cap;
    a removable abutment screw moving through said elastomeric cap and the passage extending longitudinally through said flexible abutment for receipt by said existing root portion by which said flexible abutment is detachably connected to said existing root portion; and
    a locking nut coupled to and moving axially along said abutment screw for applying an outward pushing force against said flexible abutment by which to cause said elastomeric cap to be compressed against, said crown.

20. The replacement crown assembly recited in claim 19, wherein said flexible abutment includes a plurality of flexible splines, the outward pushing force applied against said flexible abutment by said locking nut causing said flexible splines to bend towards and compress said elastomeric cap against said crown.

21. The replacement crown assembly recited in claim 19, wherein a first end of said abutment screw and the interior of said locking nut are each threaded by which to enable said locking nut to be coupled to said first end and move axially therealong so as to apply said outward pushing force against said flexible abutment.

22. The replacement crown assembly recited in claim 21, wherein the opposite end of said abutment screw and the existing root portion are each threaded by which to enable said abutment screw to be coupled to said root portion for detachably connecting said flexible abutment to said root portion.

23. The replacement crown assembly recited in claim 22, wherein said abutment screw includes a relatively wide washer located between the threaded first and opposite ends thereof, said locking nut moving axially along said first end and into contact with said washer to prevent said abutment screw from leaning towards said flexible abutement.

* * * * *